United States Patent [19]

Hol et al.

[11] Patent Number: 4,808,716
[45] Date of Patent: Feb. 28, 1989

[54] 9-(PHOSPONYLMETHOXYALKYL) ADENINES, THE METHOD OF PREPARATION AND ITILIZATION THEREOF

[75] Inventors: Antonín Hol; Ivan Rosenberg, both of Praha, Czechoslovakia

[73] Assignee: Ceskoslovenska akademic ved, Czechoslovakia

[21] Appl. No.: 856,299

[22] Filed: Apr. 25, 1986

[30] Foreign Application Priority Data

Apr. 25, 1985 [CS] Czechoslovakia ............. 3017-85

[51] Int. Cl.$^4$ ............. C07D 9/65; C07D 473/34
[52] U.S. Cl. .................. 544/244; 544/277
[58] Field of Search ............. 544/244; 514/81

[56] References Cited

U.S. PATENT DOCUMENTS 4,323,573 4/1982 Schaeffer .......... 514/81 X
4,659,825 4/1987 Holy et al. ............. 544/244

FOREIGN PATENT DOCUMENTS 0898620 5/1984 Belgium .
3400278 7/1984 Fed. Rep. of Germany ...... 544/244
2539132 7/1984 France .
WO84/04748 12/1984 PCT Int'l Appl. ............ 544/244

OTHER PUBLICATIONS

Holy, et al., Collection Czechoslovak Chem. Commun., vol. 47, pp. 3447–3463, (1982).

Benes, et al., Chemical Abstracts, vol. 104, 220678h, (1986).

Primary Examiner—Donald G. Daus
Assistant Examiner—Diana G. Rivers
Attorney, Agent, or Firm—Leydig, Voit, Mayer

[57] ABSTRACT

The invention relates to 9-(phosphonylmethoxyalkyl)adenines of the general formula I

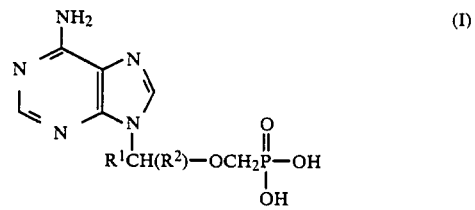

wherein $R^1$ is a hydrogen atom, and alkyl group containing one to three carbon atoms, or a hydroxymethyl group, $R^2$ is a methylene, ethylene, propylene, ethylidene, methoxyethylene, benzyloxyethylene, tetrahydropyran-2-yloxyethylene, (1-ethoxyethoxy)ethylene or 1,2-O-isopropylidene-1,2-dihydroxypropylene group the method of their preparation and utilization.

Compounds of the general formula I exhibit biological effects (e.g. antiviral) or can be converted into compounds with such effects.

2 Claims, No Drawings

9-(PHOSPONYLMETHOXYALKYL) ADENINES, THE METHOD OF PREPARATION AND UTILIZATION THEREOF

This invention relates to new 9-(phosphonylmethoxyalkyl)adenines as well as their preparation and utilization.

Phosphonylmethyl ethers of alcohols (O-substituted hydroxymethanephosphonic acids) are analogues of esters of these alcohols with phosphoric acid, differing from the latter in having a chemically and enzymatically stable ether linkage. Since phosphoric acid esters, e.g. nucleotides, phosphoglyceric acid, sugar phosphates etc., are of great importance for metabolic processes in the living matter, such analogues may also be biologically active. The said compounds can be prepared e.g. by reaction of alcohols with chloromethanephosphonic acid or its esters (E. N. Walsh, T. M. Beck, A. D. F. Toy: J. Amer. Chem. Soc. 78, 4455 (1956)) or by reaction of formals with phosphorus trichloride (U.S. Pat. No. 2,500,022) or, in case of derivatives of 1,2-diols, by reaction of these diols with chloromethanephosphonyl dichloride and subsequent alkaline hydrolysis (PV 88-83). Another method, applicable also to monohydric alcohols, is reaction of a sodium alkoxide with an ester of p-toluenesulfonyloxymethanephosphonic acid; this reaction has been used in the preparation of 5'-O-phosphonylmethyl derivatives of nucleosides (A. Hol , I. Rosenberg: Collect. Czech. Chem. Commun. 47, 3447 (1982)).

9-Alkyladenines containing one or more hydroxy groups in the alkyl chain behave as analogues of the metabolite adenosine and exhibit various biological activities (e.g. antiviral, chemosterilizing etc., see Czech. Author's Certificate No. 199093, 199094, 199095, PV 377-83, PV, 7380-83, PV 970-84). Therefore, phosphonylmethyl ethers of these compounds can be regarded as so-called acyclic analogues of adenine nucleotides. Some of these compounds show also a chemosterilizing effect in insects (Czech. Author's Certificate No. 233 655).

This invention relates to 9-(phosphonylmethoxyalkyl)adenines of the general formula I.

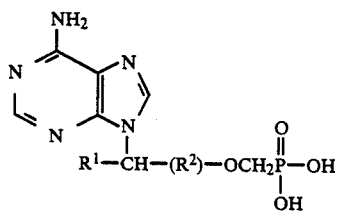

wherein $R^1$ is an atom of hydrogen, methyl or a hydroxymethyl group, $R^2$ is a methylene, ethylene, propylene, ethylidene, benzyloxyethylene, tetrahydropyran-2-yloxyethylene, 1-(ethoxyethoxy)ethylene or 1,2-O-isopropylidene-1,2-dihydroxypropylene group and the salts thereof with alkali metals, ammonia or amines.

Further, the invention relates to the method of preparing compounds of the general formula I, characterized in that 9-hydroxyalkyladenines of the general formula II

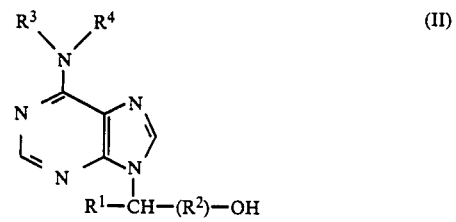

wherein $R^1$ and $R^2$ have the same signification as in the formula I, $R^3$ is a benzoyl group, $R^4$ is a hydrogen atom or a benzoyl group, or both $R^3$ and $R^4$ together are a dimethylaminomethylene group, are brought into a reaction with 1 to 2 equivalents (relative to compound II) of sodium hydride in a dipolar aprotic solvent, preferably dimethylformamide, and with 1 to 2 molar equivalents of an ester of p-toluenesulfonyloxymethanephosphonic acid of the general formula III,

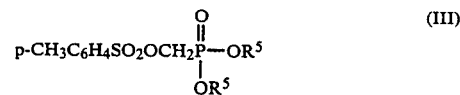

wherein $R^5$ is a methyl or ethyl group, at temperatures 0° C. to 100° C., whereupon the mixture is worked up in an alkaline aqueous or aqueous-alcoholic medium and products of the general formula IV

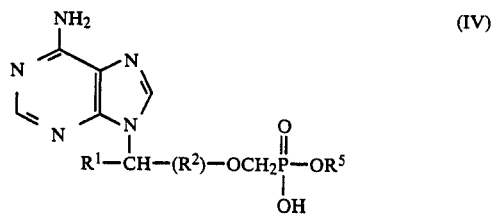

wherein $R^1$, $R^2$ and $R^5$ have the same signification as in the formula I and III, are isolated by chromatography, preferably on an ion-exchanging resin or hydrophobized silica gel, treated with a solution of trimethyliodosilane in dimethylformamide at temperatures 0° C. to 50° C., and the compounds of the general formula I are isolated by chromatography, preferably on an ion-exchanging resin or hydrophobized silica gel.

The starting compounds of the general formula II are accessible by reactions of suitably activated alcohols (e.g. tosyl or mesyl derivatives) or alkyl halides with salts of adenine, usually in dimethylformamide (see e.g. A. Hol : Collect. Czech. Chem. Commun. 43, 3444 (1978); 44, 593 (1979); 43, 3103 (1978); 43, 2054 (1978)).

The method of preparing the compounds according to this invention is based on formation of sodium salts of 9-hydroxyalkyladenine of the general formula II which contain an isolated hydroxy group. In order to prevent reaction of sodium hydride, used in the preparation of the salts, with other functionalities in the molecule, particularly those bonded to the heterocyclic adenine base, it is necessary to protect them with aroyl (benzoyl) groups or preferably with the N-dimethylaminomethylene group which can be easily introduced by reaction with the so-called dimethylformamide acetals (dialkoxymethyldimethylamines). The salts of thus-protected starting compounds of the formula II are prepared by addition of an equivalent amount or a slight excess of sodium hydride to a solution of compounds II in a solvent which does not react with sodium hydride, preferably dimethylformamide.

These salts of compounds of the general formula II are then condensed with tosylates of the general formula III which are easily accessible from diesters or triesters of phosphoric acid (Czech. Author's Certificate No. 220713, 220714). The compounds of the formula III are used in a slight excess relative to compounds of the formula II in order to eliminate possible side reactions. The condensation is carried out at room or slightly elevated temperature under strictly anhydrous conditions.

The reaction mixtures are worked up simply by dilution with water. The arising alkaline medium removes the protecting groups (aroyl or dimethylaminomethylene) together with one of the two groups bonded to the phosphonic acid by ester bonds. The arising monophosphonates of the general formula IV are not hydrolyzed further and can be easily isolated from the mixture, preferably by deionization of the adenine derivatives on strongly acidic ion-exchangers. Compounds of the general formula IV, obtained by desalting, are purified by chromatography, e.g. on an anion-exchanging resin or octadecyl-silica gel.

In the reaction with trimethyliodosilane, dried compounds of the formula IV are dissolved in dimethylformamide and mixed with the reagent (or its solution in dimethylformamide). The amount of the reagent taken is at least twice of that calculated for the number of equivalents of compound IV (taking into account all the hydroxy or amino groups present in its molecule). (Trimethyliodosilane can be also prepared in situ by reaction of trimethylchlorosilane with sodium, lithium or potassium iodidesin dimethylformamide.) The reaction of compounds of the formula IV with trimethyliodosilane is carried out under anhydrous conditions, the reaction time being usually 18–24 hours at room temperature. The reaction mixture is then decomposed by addition of a neutral or weakly alkaline buffer, e.g. the volatile triethylammonium hydrogen carbonate, and compounds of the general formula I are desalted, preferably using a medium acidic cation-exchanging resin from which, after removal of the salts, they are eluted with a volatile base such as aqueous ammonia. Compounds of the formula I are purified by chromatography on anion-exchanging resins in neutral or acidic medium, or on octadecyl-silica gel.

Compounds of the general formula I and V can be stored as free acids or their salts, prepared either by exact neutralization of the free acids or conversion of their ammonium salts into alkali metal salts using cation-exchanging resins in the appropriate form. The advantage of the last-mentioned salts (sodium and lithium salts) is their good solubility in water.

The method of preparing compounds of the formula I according to the invention can be used also for preparation of individual isomers of phosphonylmethoxyalkyladenines derived from di- or trihydroxyalkyladenines, i.e. when the mentioned preparation of these compounds by reaction with chloromethanephosphonyl chloride followed by alkaline hydrolysis (Czech Author's Certificate No. 233 655) leads to a mixture of isomers which have to be separated. In such cases the reaction is performed with a dihydroxy- or trihydroxyalkyladenine, protected on the adenine ring with a benzoyl or dimethylaminomethylene group, and with suitable alkali-stable groups, such as an acetal grouping or a benzyl group, on all the side-chain hydroxy groups except the one which shall react according to this invention. Isolated hydroxy groups can be protected preferably with tetrahydropyran-2-yl or 1-ethoxyethyl group, cis-diol groupings as isopropylidene or ethoxymethylene derivatives. Also other groups, resistant to sodium hydride, such as substituted silyl groups (tert-butyldimethylsilyl) or groups of the benzyl or trityl type, can be used. After the reaction with trimethyliodosilane, the crude compounds of the general formula I are stripped of the mentioned protected groups using a suitable procedure, such as acid hydrolysis, hydrogenolysis in an acid medium, or treatment with fluorides.

Some compounds of the general formula I which are the subject of this invention, are important active components of antiviral drugs. An example of such compound is 9-phosphonylmethoxyethyladenine which exhibits a specific activity against DNA-viruses and Moloney sarcoma (PV 3018-85). Other compounds of the general formula I can be easily converted into such biologically active compounds: e.g. 9-(3-phosphonylmethoxy-2-hydroxypropyl)adenine of the formula V ($R^1$ is H)

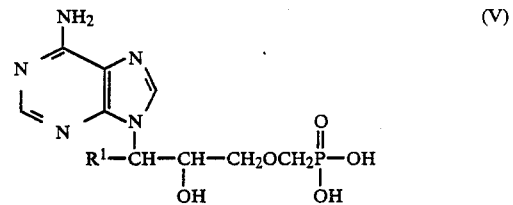

wherein $R^1$ denotes the same as in the formula I, is prepared from compounds of the formula I, where $R^2$ is a tetrahydropyran-2-yloxyethylene,(1-ethoxyethoxy)ethylene or benzyloxyethylene group by acid hydrolysis or hydrogenolysis.

The following Examples, together with the Table, illustrate the preparation and use of the new compounds of the general formula I according to this invention, without exhausting all the possibilities of the invention.

EXAMPLE 1

9-(2-Phosphonylmethoxyethyl)adenine

Sodium hydride (0.48 g; 20 mmol) is added to a solution of 9-(2-hydroxyethyl)-$N^6$-benzoyladenine (2.83 g; 10 mmol) is dimethylformamide and the mixture is stirred under exclusion of moisture (calcium chloride protecting tube) at room temperature for 20 minutes. After addition of dimethyl p-toluenesulfonyloxymethanephosphonate (2.95 g; 10 mmol) the mixture is stirred in a stoppered bottle for 48 hours at room temperature. Water (100 ml) is added and the mixture is set aside at room temperature for 15 hours. Dowex 50×8 (H+ form) is added until the mixture has acid reaction and the suspension is applied on a column of the same ion-exchanging resin (200 ml). The column is washed with water until the eluate is no longer acidic and does not absorb at 260 nm, and then with dilute (1:10, vol/vol) ammonia. Fractions, absorbing at 260 nm, are taken down at 40° C./2 kPa, and the residue is dissolved in water (10 ml) and adjusted to pH 9–10 with ammonia. This solution is applied on a column of Sephadex A-25 (HCO3 form; 100 ml) and the column is washed with water until the eluate no longer absorbs at 260 nm: Then the material is eluted by a linear gradient of triethylammonium hydrogen carbonate (prepared from 1 liter of water and 1 liter of 0.2 mol $1^{-1}$ of the mentioned buffer). The fractions, containing the principal UV-absorbing portion of the eluate, are pooled and taken down at 40° C./2 kPa. The residue is twice coevaporated with ethanol (50 ml) and the obtained compound of the formula IV (triethylammonium salt) is dried over phosphorus pentoxide at room temperature and 13 Pa for 24 hours. Yield, 70%.

This material is dissolved in dimethylformamide (70 ml) and trimethyliodosilane (12 g; 60 mmol) is added at 0° C. with magnetic stirring. After stirring in a stoppered flask at room temperature overnight, 2 mol $1^{-1}$ triethylammonium hydrogen carbonate (90 ml) is added and the mixture is heated to 60° C. for 3 hours. Water (700 ml) is added, the mixture is extracted three times with chloroform (100 ml), the aqueous phase is evaporated at 40° C./2 kPa and the residue is coevaporated with ethanol ($3 \times 100$ ml). The residue is again deionized on a column of Dowex $50 \times 8$ (H+ form; 200 ml) as described above. The crude compound I in water (20 ml) is adjusted to pH 9–10 with ammonia, and applied on a column of Dowex $1 \times 2$ (100 ml; acetate form). After washing with water, the column is eluted with a linear gradient of acetic acid (made from 1 liter of water and 1 liter of 1 mol $1^{-1}$ acetic acid). The fractions of the main UV-absorbing portion of the eluate are combined, evaporated at 40° C./2 kPa, and the acetic acid is removed by repeated evaporation with water ($3 \times 50$ ml). The residue is mixed with ethanol (5 ml) and then with ether (100 ml) and the crystalline product is filtered, washed with ether and dried in vacuo, affording 1.15 g (60% based on compound of the formula IV) of 9-(2-phosphonylmethoxyethyl)adenine, not melting up to 260° C. For $C_8H_{12}N_5O_4$ (273.3)

calculated: 35.16% C, 4.43% H, 25.63% N, 11.36% P; found: 34.84% C, 4.50% H, 25.33% N, 11.40% P.

The characteristics of this compound are given in Table 1 under No. 1. According to Example 1, also 9-(1-phosphonylmethoxy-3-hydroxy-2-propyl)adenine (No. 10) an 9-(3-phosphonylmethoxypropyl)adenine (No. 3) were prepared.

EXAMPLE 2

9-(3-Phosphonylmethoxy-2-methoxypropyl)adenine

Dimethylformamide dimethylacetal (15 ml) is added to a suspension of 9-(3-hydroxy-2-methoxypropyl)adenine (1.12 g; 5 mmol) in dimethylformamide (25 ml). The mixture is stirred at room temperature in a stoppered flask for 15 hours and then evaporated at 40° C./13 Pa. After addition of 50% aqueous pyridine (50 ml) and solid carbon dioxide (50 g), the mixture is stirred for 30 minutes, again evaporated at 40° C./13 Pa, dried by repeated coevaporation with pyridine ($3 \times 50$ ml) and then with dimethylformamide (25 ml) under the same conditions. This crude $N^6$-dimethylaminomethylene derivative is dissolved in dimetylformamide (50 ml) and sodium hydride (0.24 g; 10 mmol) is added. The subsequent reaction and work-up procedure is the same as described in Example 1 and affords 0.80 g (50%) of free 9-(3-phosphonylmethoxy-2-methoxypropyl)adenine, not melting up to 260° C. For $C_{10}H_{16}N_5O_5P$ (317.3) calculated: 37.85% C, 5.08% H, 22.07% N, 9.78% P; found: 37.50% C, 5.24% H, 22.15% N, 9.54% P. The characteristics of this compound (No. 5) are given in Table 1.

According to Example 2 were prepared 9-(2-phosphonylmethoxypropyl)adenine (No. 2) and 9-(4-phosphonylmethoxybutyl)adenine (No. 4).

EXAMPLE 3

9-(2-Benzyloxy-3-phosphonylmethoxypropyl)adenine

Dimethylformamide dimethylacetal (15 ml) is added to a solution of 9-(2-benzyloxy-3-hydroxypropyl)adenine (1.5 g; 5 mmol) in dimethylformamide (25 ml) and the desired $N^6$-dimethylaminomethylene derivative is isolated as described in Example 2. Further reaction and processing are executed in the same manner as in Example 2 except that diethyl p-toluenesulfonyloxymethanephosphonate (1.60 g; 5 mmol) is used instead of dimethyl p-toluenesulfonyloxymethanephosphonate. After treatment of the reaction mixture with water and evaporation in vacuo, the residue is heated with concentrated aqueous ammonia (25 ml) to 50° C. for 5 hours, evaporated at 40° C./2 kPa and applied on a column of octadecyl-silica gel (30μ; 90 ml) in water. The material is eluted with a linear gradient of methanol using 1 liter of water and 1 liter of 20% (vol) aqueous methanol. The principal UV-absorbing fractions are combined, taken down at 40° C./2 kPa and the thus-obtained ammonium salt of compound of the formula IV (4 mmol; 80%) is further treated with trimethyliodosilane as described in Example 1. After treatment of the reaction mixture with buffer and extraction with chloroform, the residue after evaporation of the main portion is again chromatographed on a column of octadecyl-silica gel (90 ml) under the above-described conditions. The remaining triethylammonium salt of the compound of the formula I is dissolved in water (5 ml), applied on a column of Dowex $50 \times 8$ (Li+ form; 20 ml) and eluted with water. The UV-absorbing fractions are taken down at 40° C./2 kPa, the residue is coevaporated with ethanol and mixed with ethanol (5 ml). Upon addition of ether (100 ml), the precipitate is filtered, washed with ether and dried at 13 Pa, affording 1.14 g (70% based on compound of the formula IV) of lithium salt of 9-(2-benzyloxy-3-phosphonylmethoxypropyl)adenine whose characteristics are given in Table 1 (No. 8).

EXAMPLE 4

2',3'-O-Isopropylidene-(L-threo)-9-(4-phosphonylmethoxy-2,3-dihydroxybutyl)adenine 2',3'-O-Isoproylidene-L-threo-9-(2,3,4-trihydroxybutyl)adenine (1.4 g; 5 mmol) is converted to the $N^6$-dimethylaminomethylene derivative according to Example 3 and the reaction is carried out with 0.24 g (10 mmol) of sodium hydride and 1.5 g (5 mmol) of dimethyl p-toluenesulfonyloxymethanephosphonate as described in Example 1. The isolation of the compound of the formula IV, its reaction with trimethyliodosilane and the subsequent isolation of compound of the formula I are performed as described in Example 3, affording 3.6 mmol (72%) of lithium salt of compound I whose characteristics are given in Table 1 (No. 9).

According to Example 4 were prepared 9-(3-phosphonylmethoxy-2-tetrahydropyranyloxypropyl)adenine (lithium salt, No. 6) and 9-(3-phosphonylmethoxy-2-(1-ethoxyethyl)oxypropyl)adenine (lithium salt, No. 7).

EXAMPLE 5

9-(3-Phosphonylmethoxy-2-hydroxypropyl)adenine

A solution of lithium salt of 9-(3-phosphonyloxymethoxy-2-tetrahydropyranyloxypropyl)adenine (1 mmol) in 0.25 mol $l^{-1}$ sulfuric acid (20 ml) was kept at 40° C. for 18–24 hours, diluted with water (100 ml) and neutralized with saturated solution of barium hydroxide. The suspension was heated to 80° C. for 30 min and filtered through Celite. The filtrate was concentrated at 40° C./2 kPa to about 20 ml, this solution was applied on a column of Dowex 50×8 ($Na^+$ form; 20 ml) and eluted with water. The UV-absorbing eluate was evaporated at 40° C./2 kPa, the residue was dried by coevaporation with ethanol (2×20 ml), mixed with ethanol (3 ml) and the product was precipitated with ether (100 ml). Filtration, washing with ether and drying at 13 Pa gave 80% of sodium salt of 9-(3-phosphonylmethoxy-2-hydroxypropyl)adenine, whose characteristics are given in Table 1 (No. 11).

9-(3-Phosphonylmethoxy-2-hydroxypropyl)adenine (No. 11) was prepared according to Example 5 also from lithium salt of 9-(3-phosphonylmethoxy-2-(1-ethoxyethyl)oxypropyl)adenine (No. 7). The procedure was also applied to the preparation of 9-(L-threo)-(4-phosphonylmethoxy-2,3-dihydroxybutyl)adenine (No. 12) from the 2′,3′-O-isopropylidene derivative (No. 9).

EXAMPLE 6

9-(3-Phosphonylmethoxy-2-hydroxypropyl)adenine

To a solution of lithium salt of 9-(3-phosphonyloxymethoxy-2-benzyloxypropyl)adenine (No. 8; 1 mmol) in methanol (50 ml) were added subsequently 10% palladium on charcoal (0.50 g), 30% palladium chloride (0.5 ml) and hydrochloric acid (0.3 ml). After flushing the hydrogenation vessel three times with hydrogen, the mixture is stirred in a hydrogen atmosphere (0.1 MPa overpressure) at room temperature for 16–24 hours. The mixture is filtered through Celite, made alkaline with ammonia and evaporated to dryness. The residue, dissolved in water (5 ml), is applied on a column of Dowex 50×8 ($H^+$ form; 50 ml). After washing with water (300 ml), the product is eluted with 2.5% ammonia solution. The UV-absorbing fractions are evaporated to dryness at 40° C./2 kPa and the residue is converted into the lithium salt as described in Example 3, affording 75–80% of product identical with the lithium salt prepared according to Example 5.

EXAMPLE 7

Primary rabbit kidney cells grown in Eagle's essential medium are infected for 1 hour with $10^{4.5}$ PFU/0.5 ml (PFU denotes a plaque formation unit) of herpes simplex virus, type 1 (KOS strain). Then the medium is replaced by a solution of compound of the formula I, where $R^1$ is an hydrogen atom and $R^2$ is a methylene group (compound No. 1 in Table 1), in Eagle's essential medium (concentration, 100 μg I/ml medium). After incubation for 48 hours at 37° C., the yield of the virus is determined by plaque formation in the PRK cells. A control experiment is carried out in the same manner but the culture is incubated only in Eagle's essential medium. Under these conditions the virus titre decreases 14,500 times (Δ log PFU/ml=3.16).

EXAMPLE 8

Primary rabbit kidney cells in Petri dishes are infected with herpes simplex virus, type 2 (G-strain), in a dose hundred times larger than that necessary for inducing 50% of the cytopathic effect of the virus. After 1 hour the cells are incubated with increasingly concentrated solutions of the compounds in Eagle's essential medium for 24 hours at 37° C. The cytopathic effect of the virus is determined as described in "Tissue culture", Pergamon Press, New York 1973, p. 510. Under these conditions, compounds of the formula I, No. 1 and 12 in Table 1, show a 50% inhibition of the cytopathic effect of HSV-2 virus in concentration 7 μg/ml.

TABLE 1

Characteristics of the compounds according to the invention

| | | | IV | | | I | |
|---|---|---|---|---|---|---|---|
| No. | $R^1$ | $R^2$ | Yield % | $R_F^a$ | $R_{Up}^b$ | Yield % | $R_F^a$ | $R_{Up}^b$ |
| 1 | H | $CH_3$ | 70 | 0.45 | 0.45 | 60 | 0.11 | 0.82 |
| 2 | H | $CH(CH_3)$ | 75 | 0.50 | 0.42 | 80 | 0.18 | 0.80 |
| 3 | H | $CH_2CH_2$ | 72 | 0.50 | 0.42 | 67 | 0.18 | 0.80 |
| 4 | H | $CH_2CH_2CH_2$ | 75 | 0.54 | 0.40 | 70 | 0.24 | 0.81 |
| 5 | H | $CH(OCH_3)CH_2$ | 78 | 0.55 | 0.40 | 64 | 0.25 | 0.78 |
| 6 | H | $CH(O\text{-tetrahydropyranyl})CH_2$ | 80 | 0.57 | 0.40 | 67 | 0.35 | 0.78 |
| 7 | H | $CH(OCHOC_2H_5)CH_2$ with $CH_3$ | 70 | 0.57 | 0.38 | 70 | 0.35 | 0.76 |
| 8 | H | $CH(OCH_2C_6H_5)CH_2$ | 80 | 0.70 | 0.35 | 70 | 0.42 | 0.72 |
| 9 | H | $CH\text{-}CH\text{-}CH_2$ with isopropylidene-dioxy | 80 | 0.60 | 0.40 | 90 | — | 0.75 |
| 10 | $CH_3$ | $CH_2$ | 75 | 0.52 | 0.40 | 70 | 0.18 | 0.78 |
| 11 | $HOCH_2$ | $CH_2$ | 70 | 0.47 | 0.40 | 60 | 0.12 | 0.80 |
| 12 | H | $CH(OH)CH_2^c$ | — | — | — | 80 | 0.10 | 0.82 |

TABLE 1-continued

| | | | Characteristics of the compounds according to the invention | | | | | |
| | | | IV | | | I | | |
| No. | R[1] | R[2] | Yield % | $R_F{}^a$ | $R_{Up}{}^b$ | Yield % | $R_F{}^a$ | $R_{Up}{}^b$ |
| --- | --- | --- | --- | --- | --- | --- | --- | --- |
| 13 | H | CH(OH)CH(OH)CH$_2$ | — | — | — | 85 | 0.10 | 0.82 |

[a] Paper chromatography in the system 2-propanol - conc. aqueous ammonia - water (7:1:2);
[b] paper electrophoresis (20 V/cm) in 0.1 mol l$^{-1}$ triethylammonium hydrogen carbonate;
[c] compound of the formula V.

What we claim is:

1. A 9-(phosphonylmethoxyalkyl)adenine having the formula I

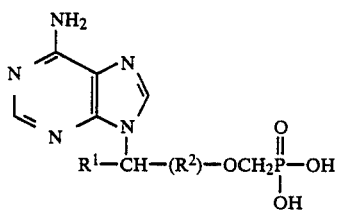

wherein R[1] is hydrogen and R[2] is selected from the group consisting of methylene, ethylene, propylene, ethylidene, and 1,2-O-isopropylidene-1,2-di-hydroxypropylene; and the salts thereof with alkali metals or ammonia.

2. A 9-(phosphonylmethoxyalkyl)adenine of the formula

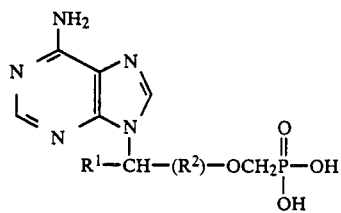

wherein R[1] is selected from the group consisting of methyl and hydroxymethyl and R[2] is selected from the group consisting of methylene, ethylene, propylene, ethylidene, methoxyethylene, benzyloxyethylene, tetrahydropyranyl-2-oxyethylene, (1-ethoxyethoxy)ethylene and 1,2-O-isopropylidene-1,2-dihydroxypropylene; and the salts thereof with alkali metals or ammonia.

* * * * *